(12) United States Patent
Lauer

(10) Patent No.: US 8,133,516 B2
(45) Date of Patent: Mar. 13, 2012

(54) THERAPEUTIC ULTRASOUND GEL

(76) Inventor: Scott D. Lauer, Colleyville, TX (US)

( * ) Notice: Subject to any disclaimer, the term of this patent is extended or adjusted under 35 U.S.C. 154(b) by 85 days.

(21) Appl. No.: 12/588,763

(22) Filed: Oct. 27, 2009

(65) Prior Publication Data

US 2010/0112065 A1      May 6, 2010

Related U.S. Application Data

(60) Provisional application No. 61/193,160, filed on Oct. 31, 2008.

(51) Int. Cl.
*A61K 36/886* (2006.01)
(52) U.S. Cl. ......................................................... 424/744
(58) Field of Classification Search .................. None
See application file for complete search history.

(56) References Cited

U.S. PATENT DOCUMENTS

| | | | |
|---|---|---|---|
| 5,882,666 A | 3/1999 | Averill et al. | |
| 5,928,659 A | 7/1999 | Moy | |
| 6,261,574 B1 * | 7/2001 | Costello | 424/400 |
| 6,495,126 B1 * | 12/2002 | Schiltz | 424/78.02 |
| 6,855,117 B2 | 2/2005 | Skover | |
| 2002/0120225 A1 | 8/2002 | McDaniel | |
| 2004/0018244 A1 * | 1/2004 | Piterski | 424/535 |
| 2004/0265387 A1 | 12/2004 | Hermeling et al. | |
| 2005/0215908 A1 * | 9/2005 | Chew et al. | 600/459 |
| 2006/0040252 A1 | 2/2006 | Mitts et al. | |
| 2006/0194754 A1 | 8/2006 | de Jong et al. | |
| 2006/0198800 A1 * | 9/2006 | Dilallo et al. | 424/59 |
| 2006/0247377 A1 | 11/2006 | Riegel et al. | |
| 2007/0078290 A1 | 4/2007 | Esenaliev | |
| 2007/0280898 A1 * | 12/2007 | Riddle | 424/74 |

* cited by examiner

*Primary Examiner* — Christopher R. Tate
*Assistant Examiner* — Deborah A. Davis
(74) *Attorney, Agent, or Firm* — Richard C. Litman

(57) ABSTRACT

The therapeutic ultrasound gel is a composition that lubricates the abdomen for ultrasound scanning, that enhances the transmission of sound waves during ultrasound diagnostic imaging, and that has beneficial therapeutic effects in preventing the formation of stretch marks. The composition contains effective amounts of *aloe vera* (*Aloe barbadensis*), glycerin, and various agents for preventing the formation of stretch marks, with the balance being sufficient water to adjust the consistency of the composition. The composition may also be formulated for home use, chiefly by the addition of vitamin D3 or, alternatively, vitamin K. Either formulation may contain additional excipients, including surfactants, emulsifiers, humectants, stabilizers, thickeners, pH balancers, preservatives, colorants, and scent, if desired.

14 Claims, No Drawings

THERAPEUTIC ULTRASOUND GEL

CROSS-REFERENCE TO RELATED APPLICATION

This application claims the benefit of U.S. Provisional Patent Application Ser. No. 61/193,160, filed Oct. 31, 2008.

BACKGROUND OF THE INVENTION

1. Field of the Invention

The present invention relates to lubricants used for medicinal purposes and to skin care compositions, and particularly to a therapeutic ultrasound gel used as a lubricant during ultrasonography procedures that enhances the transmission of sound waves and that also helps to prevent the formation of stretch marks.

2. Description of the Related Art

Ultrasonography is a diagnostic technique that uses ultrasound scanning to produce images on a cathode ray tube or television screen. It is widely used in obstetrics for several purposes, including confirming pregnancy under circumstances where hormonal tests cannot be used, for establishing gestational age and the number of fetuses, for determining sex of the fetus, for detecting fetal abnormalities or fetal death, for monitoring fetal growth, as an adjunct to amniocentesis, etc. Ultrasound Doppler scanning may also be used to test fetal blood flow. Ultrasonography is a valuable technique, since it provides a safe alternative to roentographic or X-ray techniques.

The procedure typically will involve the application of a gel to the patient's abdomen. A piezoelectric transducer that generates sound waves at a frequency in the range of 2.25 to 7.0 MHz is placed in the gel and moved across the abdomen to form images at different angles. The sound waves reflect off tissues to produce an echo signal that can be converted to images that can be viewed on a screen and interpreted by a competent medical practitioner. The gel lubricates the abdomen and prevents the sound waves from being trapped or reflected by air pockets that might distort the image and lead to an incorrect diagnosis. Typically, after completion of the ultrasound examination, any remaining gel is wiped off the patient's abdomen. While several gels are available, there is still a need for a gel that can enhance the transmission of sound waves from the transducer into the abdominal cavity.

A common concern in pregnancy is that some pregnant women develop stretch marks or striae that never completely disappear. The striae may be purple during pregnancy, but usually turn white over a period of time after the pregnancy is resolved. Although the stretching of the abdominal skin during pregnancy is an initiating factor, it is thought that other factors may result in the skin losing its natural elasticity, with the resulting development of permanent striae that many women regard as an embarrassing disfigurement. A variety of compositions have been touted as preventing the formation of stretch marks or promoting restoration of the skin's elasticity to cosmetically heal the striae, but none have been found to be completely effective.

Thus, a therapeutic ultrasound gel solving the aforementioned problems is desired.

SUMMARY OF THE INVENTION

The therapeutic ultrasound gel is a composition that lubricates the abdomen for ultrasound scanning, that enhances the transmission of sound waves during ultrasound diagnostic imaging, and that has beneficial therapeutic effects in preventing the formation of stretch marks. The composition contains effective amounts of *aloe vera* (*Aloe barbadensis*), glycerin, and various agents for preventing the formation of stretch marks, with the balance being sufficient water to adjust the consistency of the composition. The composition may also be formulated for home use, chiefly by the addition of vitamin D3 or, alternatively, vitamin K. Either formulation may contain additional excipients, including surfactants, emulsifiers, humectants, stabilizers, thickeners, pH balancers, preservatives, colorants, and scent, if desired.

The agents for preventing stretch marks may include antioxidants, such as grapefruit seed extract, and vitamins E and C; collagen and elastin formation and matrix agents, including hyaluronic acid, pentapeptides and tripeptides, and vitamin A palmitate; antiinflammatory agents, such as licorice root and panthenol (vitamin B5); and fatty acids, such as lecithin, phospholipids, and squalane, to aid in transport of active ingredients through the skin.

These and other features of the present invention will become readily apparent upon further review of the following specification.

DETAILED DESCRIPTION OF THE PREFERRED EMBODIMENTS

The ultrasound therapeutic gel is a composition that lubricates the abdomen for ultrasound scanning, that enhances the transmission of sound waves during ultrasound diagnostic imaging, and that has beneficial therapeutic effects in preventing the formation of stretch marks. The composition contains effective amounts of *aloe vera* (*Aloe barbadensis*), glycerin, and various agents for preventing the formation of stretch marks, with the balance being sufficient water to adjust the consistency of the composition.

As used herein, the terms "prevention" or "preventing" mean one or more effects that include the complete absence of the formation of stretch marks; prophylaxis of stretch marks; inhibiting the formation of stretch marks; hindering the formation of stretch marks; having a tendency to reduce the incidence, number, size, discoloration, or severity of stretch marks; or a reduction in the loss of skin elasticity resulting from or associated with stretch marks.

The composition contains *Aloe vera* (also known as *Aloe barbadensis* and *Aloe vulgari*), which is an anti-inflammatory agent. *Aloe vera* is a succulent plant of the Lily family that is native to Africa and grown commercially in warm regions throughout the world. The inner layer of the plant leaf contains a clear gel. *Aloe vera* gel is known to contain a number of antiinflammatory agents useful for topical applications. The gel produces antiinflammatory, moisturizing and emollient effects that help to relieve pain and stop itching. *Aloe vera* dilates capillaries allowing more blood to get to the diseased area, thus speeding up the healing process. The ultrasound therapeutic gel may be prepared either by using the *aloe vera* gel itself, or an extract of *aloe vera* that is blended with glycerin, polysorbate 20 (well known surfactant or emulsifier) or other surfactant or emulsifier, and water to a consistency that provides a suitable lubricant for the ultrasound transducer, and that also enhances the transmission of sound waves during ultrasonography. When the *aloe vera* gel is used, the *aloe vera* may constitute a higher proportion of the ingredients (e.g., about 70% by weight) than when the *aloe vera* extract is used. Representative proportions of the ingredients are shown in Table I, below.

The agents for preventing stretch marks may include antioxidants, such as grapefruit seed extract, and vitamins E and C; collagen and elastin formation and matrix agents, including hyaluronic acid, pentapeptides and tripeptides, and vitamin A palmitate; antiinflammatory agents, such as licorice root and panthenol (vitamin B5); and fatty acids, such as lecithin, phospholipids, and squalane, to aid in transport of active ingredients through the skin. The agents for preventing stretch marks may constitute up to 5% by weight of the composition.

The body requires oxygen for proper cell metabolism. Nevertheless, the body may have too much oxygen, which may be present in harmful forms, including free radicals, such as $O_2-$, peroxides, and hydroxyl radials. Free radicals are highly reactive and damage the connective tissue and the blood vessels. Antioxidants neutralize free radicals, either by reducing them directly, or by an addition reaction in which the antioxidant is oxidized by the free radicals to incorporate the additional oxygen into their structure.

The ultrasound therapeutic gel includes the antioxidants grapefruit seed extract, vitamin E, and vitamin C, or at least one of the antioxidants. Grapefruit seed extract is derived from the seeds, pulp, and white membranes of the grapefruit, which are preferably extracted in glycerin and water. The extract has antioxidant properties, containing bioflavonoids, vitamin C, vitamin E, and other constituents.

The composition contains vitamin E (alpha-tocopherol or tocopherol acetate), which is reported to have antiinflammatory effect when applied topically. Vitamin E, which may be marketed as α-tocopherol or as mixed tocopherols, is also an antioxidant. Studies have also shown that vitamin E appears to work synergistically with vitamin C, so that vitamin E helps to maintain vitamin C levels, and vice versa.

Vitamin C (ascorbic acid) is also an antioxidant. Vitamin C is also known to strengthen capillaries and cell walls, and is crucial to the formation of collagen. Vitamin C may work synergistically with the grapefruit seed extract, and is known to work synergistically with vitamin E. The other antioxidants may serve to protect vitamin C, thereby enabling the vitamin C to perform its role in forming collagen in order to strengthen the blood vessels.

The ultrasound therapeutic gel contains collagen and elastin formation and matrix agents, including hyaluronic acid, pentapeptides and tripeptides, and vitamin A palmitate, or at least one such collagen and elastin formation and matrix agent. Hyaluronic acid is naturally found as part of the connective tissue matrix layer of the dermis, along with the fibers collagen and elastin. Hyaluronic acid hydrates the skin, transports essential nutrients to the skin, and adds volume, thereby contributing to the skin's healthy appearance, so that it is often used in skin care products. Polypeptides, such as pentapeptides and tripeptides, or docrin or proteoglycan analogs, form part of the building blocks for restoring collagen and elastin fibers, which are damaged by stretch marks during pregnancy.

Vitamin A palmitate (retinyl palmitate) is the ester of retinol (vitamin A) and palmitic acid. After absorption through the skin, retinyl palmitate is converted to retinol, and then to retinoic acid. Tretinoin (3,7,-dimethyl-9-(2,6,6-trimethyl-1-cyclohexenyl)-nona-2,4,6,8-tetraenoic acid) is the all-trans retinoic acid that is the active form of vitamin A in a medication sold by Johnson & Johnson under the trade name Retin-A. Retin-A is sold as a cream for the treatment of acne, and is also a common component in skin care compositions that claim to reduce aging and remove wrinkles.

It has also been reported, e.g., on the NHS web site in the United Kingdom, that Retin-A has been used to treat stretch marks. However, Retin-A is not effective for old stretch marks, but only new stretch marks that are still pink or red in color. It is thought that Retin-A enhances the growth of collagen and elastin, so that the skin regains its elasticity. It is cautioned, however, that Retin-A should not be used by women who are pregnant or who are breastfeeding, apparently because of the risk of birth defects and transmission to the baby. See, e.g., the stretchmarkcure.com web site. It is believed, however, that the quantity of vitamin A palmitate in the ultrasound therapeutic gel, shown in Tables I and II, is within safe limits.

The ultrasound therapeutic gel also includes antiinflammatory agents, such as licorice root and pantothenol (vitamin B5), or at least one antiinflammatory agent. Licorice root contains glycyrrhizin, which, when hydrolyzed, produces glycyrrhetinic acid. Topical preparations containing glycyrrhetinic acid have been used for the treatment of eczema, psoriasis, and other skin irritations, where it exerts an antiinflammatory effect similar to hydrocortisone, as in the ultrasound therapeutic gel. Vitamin B5 (pantothenic acid, or its more stable derivatives, pantothenol and calcium pantothenate) may also be used for its antiinflammatory effect in deterring skin irritation.

The ultrasound therapeutic gel also contains fatty acids, or at least one fatty acid, such as lecithin, phospholipids, and squalane, to aid in transport of active ingredients through the skin. Lecithin is a fatty substance that is normally present in the diet and performs essential functions for every cell in the body. In the ultrasound therapeutic gel, lecithin serves to transport other active ingredients through cell membranes. Phospholipids perform a similar function. Squalane may be derived from shark liver oil, olive oil, amaranth seed oil, rice bran oil, or wheat germ oil. Squalane is also a source of fatty acids that, in the ultrasound therapeutic gel, serve to transport other active ingredients through cell membranes, and particularly through the skin.

The ultrasound therapeutic gel may also include excipients conventionally found in topical preparations, including humectants, such as caprylyl/carpyryl glucoside and caprylyl glycol; natural thickening agents, such as xanthan gum, for increasing viscosity, preventing creaming, and stabilizing colloidal oils; synthetic thickening agents, such as carbomer, an acrylic acid-based emulsion stabilizer; and a pH balancer, such as triethanolamine. A preferred pH for the composition may be between 6 and 7.2.

Table I provides an exemplary composition, with the quantity of each ingredient expressed as a percentage weight/volume.

TABLE I

Ultrasound Gel Formulation

| Component | Quantity (wt/vol) |
|---|---|
| *Aloe Barbadensis* Leaf Extract | 20 to 70% |
| Glycerin | 20 to 70% |
| Polysorbate 20 | 0.5-2.0% |
| Hyaluronic Acid | 0.5-2.0% |
| Grapefruit Seed Extract | 0.1-0.5% |
| Licorice Root Extract | 0.1-0.5% |
| Vitamin A Palmitate | 0.1-0.5% |
| Vitamin E (Tocopherol Acetate) | 0.1-0.5% |
| Vitamin C (Ascorbic Acid) | 0.1-0.5% |
| Lecithin, Fatty Acids, or Phospholipids | 0.1-0.5% |
| Vitamin B5 (Pantothenol) | 0.1-0.5% |
| Squalane (shark liver oil, olive oil, amaranth seed oil, rice bran oil, or wheat germ oil) | 0.1-0.5% |
| Caprylyl/Carpryl Glucoside | 0.1-0.5% |
| Caprylyl Glycol | 0.1-0.5% |
| Xanthan Gum | 0.1-0.5% |
| Carbomer | 0.1-0.5% |

TABLE I-continued

Ultrasound Gel Formulation

| Component | Quantity (wt/vol) |
| --- | --- |
| Triethanolamine | 0.1-0.5% |
| Pentapeptides and tripeptides | 0.1-0.5% |
| Water | Balance to consistency |

In use, the composition described in Table I is applied to the patient's abdomen. The ultrasound scanner is placed in contact with the gel and moved across the abdomen to take images at different angles. Upon completion of the diagnostic scanning procedure, any remaining gel is rubbed into the abdomen, where it is absorbed through the skin.

The therapeutic benefits of the ultrasound therapeutic gel in preventing and treating stretch marks may be extended by modifying the formulation to produce a composition that may continue to be applied by the patient in the privacy of her home. For this purpose, the composition need not have as much lubricity as the ultrasound formulation. Although still a gel, the composition may include an agent to thin the composition to enhance the flow, such as ethoxydiglycol, and the relative proportions of *aloe*, glycerin, and water may be adjusted to change the consistency of the gel. In addition, Vitamin D3 or Vitamin K may be added to enhance absorption of the active ingredients through the skin, and a preservative, e.g., diazolidinyl urea, may be added to prevent deterioration of the composition during storage. Further, the relative proportion of peptides may be increased to enhance the formation of collagen and elastin. An exemplary formulation for home use is shown in Table II, with the quantities provided in ranges expressed as weight to volume.

In either the ultrasound or the home use formulations, colorants and/or scent may be added for cosmetic and esthetic purposes, if desired.

TABLE III

Home Use Stretch Mark Gel Formulation

| Component | Quantity (wt/vol) |
| --- | --- |
| *Aloe Barbadensis* Leaf Extract | 20 to 70% |
| Glycerin | 20 to 70% |
| Polysorbate 20 | 0.5-2.0% |
| Ethoxydiglycol | 0.5-2.0% |
| Hyaluronic Acid | 0.5-2.0% |
| Grapefruit Seed Extract | 0.1-0.5% |
| Licorice Root Extract | 0.1-0.5% |
| Vitamin A Palmitate | 0.1-0.5% |
| Vitamin E (Tocopherol Acetate) | 0.1-0.5% |
| Vitamin C (Ascorbic Acid) | 0.1-0.5% |
| Vitamin D3 or Vitamin K | 0.1-0.5% |
| Lecithin, Fatty Acids, or Phospholipids | 0.1-0.5% |
| Vitamin B5 (Pantothenol) | 0.1-0.5% |
| Squalane (shark liver oil, olive oil, amaranth seed oil, rice bran oil, or wheat germ oil) | 0.1-0.5% |
| Caprylyl/Carpryl Glucoside | 0.1-0.5% |
| Caprylyl Glycol | 0.1-0.5% |
| Xanthan Gum | 0.1-0.5% |
| Carbomer | 0.1-0.5% |
| Triethanolamine | 0.1-0.5% |
| Pentapeptides and tripeptides | 4-6% |
| Diazolidinyl Urea | 0.1-0.5% |
| Water | Balance to consistency |

In use, the formulation described in Table II may be applied by the patient in the privacy of her home at periodic intervals. The formulation is applied to the abdomen, or to other skin areas that may be affected by stretch marks, where it is absorbed through the skin.

It is to be understood that the present invention is not limited to the embodiments described above, but encompasses any and all embodiments within the scope of the following claims.

I claim:

1. A topical gel composition for reducing the formation of stretch marks, comprising:
   aloe vera gel in an amount of from 20-70% weight of the composition;
   glycerin in an amount of from 20-70% weight of the composition;
   an effective amount of at least one agent for reducing the formation of stretch marks;
   an emulsifier; and
   water to adjust the consistency of the composition to form a gel.

2. The topical gel according to claim 1, wherein said at least one agent for reducing the formation of stretch marks comprises:
   at least one antioxidant;
   at least one collagen and elastin formation and matrix agent;
   at least one anti-inflammatory agent; and
   at least one fatty acid.

3. The topical gel according to claim 2, wherein said at least one antioxidant is selected from the group consisting of grapefruit seed extract, vitamin E, and vitamin C.

4. The topical gel according to claim 2, wherein said at least one collagen and elastin formation and matrix agent is selected from the group consisting of hyaluronic acid, pentapeptides, tripeptides, and vitamin A palmitate.

5. The topical gel according to claim 2, wherein said at least one anti-inflammatory agent is selected from the group consisting of licorice root and vitamin B5.

6. The topical gel according to claim 2, wherein said at least one fatty acid is selected from the group consisting of lecithin, phospholipids, and squalane.

7. The topical gel according to claim 1, wherein said emulsifier comprises xanthan gum.

8. The topical gel according to claim 1, wherein said emulsifier comprises a carbomer.

9. The topical gel according to claim 1, wherein said emulsifier comprises polysorbate 20.

10. A home care composition for the treatment of stretch marks, comprising:
    the gel according to claim 1;
    a thinning agent;
    a skin transport agent selected from the group consisting of vitamin D3 and vitamin K; and
    a preservative.

11. The home care composition according to claim 10, wherein said thinning agent comprises ethoxydiglycol.

12. The home care composition according to claim 10, wherein said preservative comprises diazolidinyl urea.

13. The topical gel according to claim 1, wherein the amount of aloe vera is selected to reduce the stretch marks during ultrasonic imaging.

14. The topical gel according to claim 1, wherein the amount of aloe vera is selected to enhance the sound waves during ultrasonic imaging.

* * * * *